Figure 1:
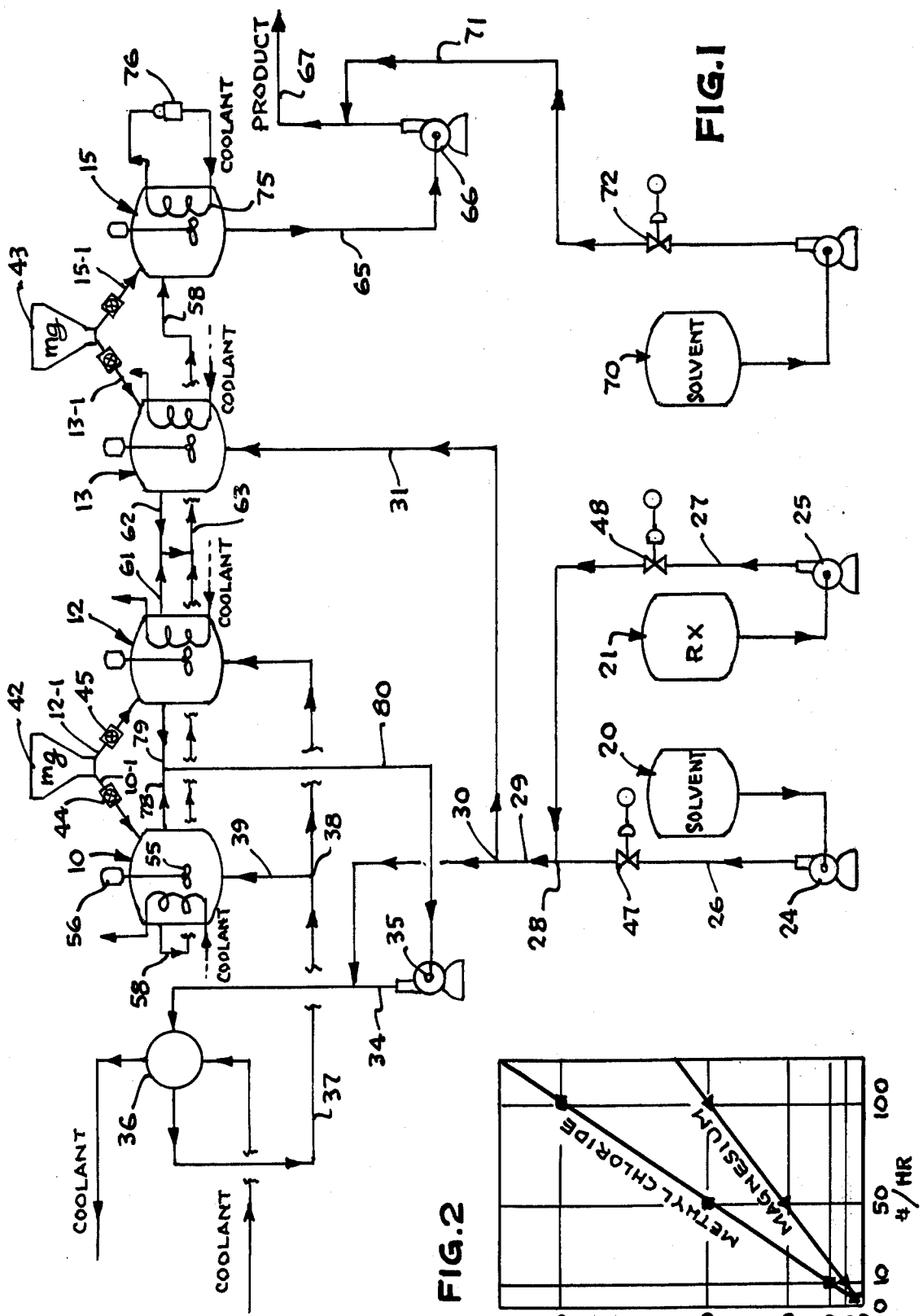

United States Patent

Blackmar et al.

[11] 4,032,298
[45] June 28, 1977

[54] APPARATUS FOR PRODUCTION OF GRIGNARD REAGENT

[75] Inventors: Guy E. Blackmar, Freeport; Robert C. Wight, Sugarland; Richard B. Smith, Freeport, all of Tex.

[73] Assignee: Nalco Chemical Company, Chicago, Ill.

[22] Filed: Dec. 30, 1974

[21] Appl. No.: 537,701

Related U.S. Application Data

[62] Division of Ser. No. 418,101, Nov. 21, 1973, Pat. No. 3,911,037.

[52] U.S. Cl. .............................. 23/260; 260/665 G
[51] Int. Cl.² ....................... B01J 8/08; C07F 3/02
[58] Field of Search .................. 23/260; 260/665 G

[56] References Cited

UNITED STATES PATENTS

| | | | |
|---|---|---|---|
| 2,414,505 | 1/1947 | Arntzen | 260/665 G X |
| 3,069,242 | 12/1962 | Brooks et al. | 23/260 |
| 3,086,849 | 4/1963 | Goldsmith | 23/260 |

*Primary Examiner*—Wilbur L. Bascomb, Jr.
*Assistant Examiner*—Barry I. Hollander
*Attorney, Agent, or Firm*—Kinzer, Plyer, Dorn & McEachran

[57] ABSTRACT

Grignard reagent is produced continuously in a reactor vessel, overflowing into a holding vessel from which the product is continuously removed; the reaction proceeds in the presence of an excess of magnesium constantly maintained, and a portion of the reacting mixture is withdrawn, circulated to a heat exchanger and returned to the reactor vessel.

3 Claims, 2 Drawing Figures

APPARATUS FOR PRODUCTION OF GRIGNARD REAGENT

This is a division of application Ser. No. 418,101, filed Nov. 21, 1973 now U.S. Pat. No. 3,911,037.

This invention relates to the production of Grignard reagents by a continuous as distinguished from a batch process.

A Grignard reagent is an organomagnesium halide compound represented chemically by the formula RMgX where R is a carbon-linked organic radical, usually an alkyl radical such as methyl ($-CH_3$) ethyl ($CH_3-CH_2-$) and so on; Mg being magnesium and X standing for a halide such as chlorine or bromine. The reagent is employed as an intermediate in organic synthesis reactions.

The Grignard system itself is much more complicated than the mere expression RMgX. For all practical purposes the system exists only as a complex in solution. The solvent is usually an ether. The real structure of the Grignard system is yet to be determined with certainty.

The reaction, in solution, proceeds as $RX + Mg \rightarrow RMgX$, an exothermic reaction which may release upwards of 1000 BTU per pound of product (solution) requiring a great deal of cooling. Additionally, the process is accompanied by the so-called Wurtz-Fittig side reaction where both magnesium and the organic reactant are wasted, forming $R_2$ and $MgX_2$. Thus, the expected side reaction consumes magnesium without producing the desired end product, meaning reduced yield from both the magnesium and the organic compound. The Wurtz-Fittig reaction is a function of Grignard and RX concentrations and temperature of solution.

The problem of exothermic reaction and reduced yield from magnesium are pronounced and lead to related problems which will be recognized from the context to follow. Accordingly, it is the primary object of the present invention to reduce the loss of magnesium due to the aforementioned side reaction by generating the Grignard reagent constantly in the presence of a constantly maintained excess of magnesium while employing one or more reaction vessels and a single surge product vessel. Thus, each reaction vessel is tapped at a level where overflow can occur into a surge product (holding) vessel and the product for use is pumped from the holding vessel to a point of delivery. By so proceeding it is possible to interrelate the flow rate of RX and Mg so that the latter is always maintained in an excess amount (3% in excess of the stoichiometric amount) and resultantly the loss of magnesium due to side reaction may be reduced from the expected 0.6% (batch operation) to less than 0.2%. Excess magnesium may always be recovered; the point is that waste or loss is reduced.

Additional and related objects of the present invention are: to develop a system for Grignard production in which a plurality of reaction vessels continuously, in parallel, generate the Grignard reagent which itself may be produced in any desired concentration at any time; to be able to constantly adjust the reaction to limit Wurtz-Fittig losses; and to conserve refrigeration compressors (and in fact allow for a selective inactive spare) which will circulate coolant necessary to extract the large BTU output of the exothermic reaction.

Other and further objects of the present invention will be apparent from the following description and claims and are illustrated in the accompanying drawing which, by way of illustration, shows the preferred embodiment of the present invention and the principles thereof and what is now considered to be the best mode contemplated for applying these principles. Other embodiments of the invention embodying the same or equivalent principles may be made as desired by those skilled in the art without department from the present invention.

Figure 2:
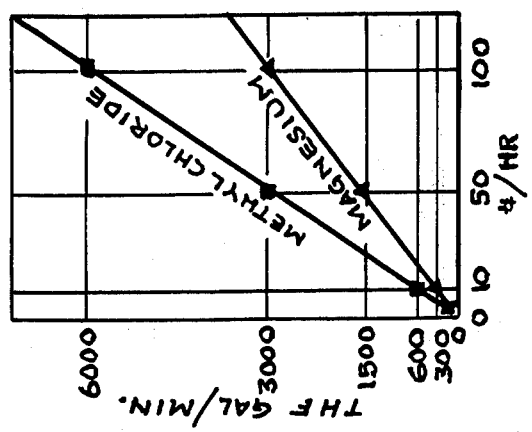

IN THE DRAWING:

FIG. 1 is a flow chart of apparatus and method of production employed under the present invention; and FIG. 2 is a graph showing consumption of reactants.

The preferred embodiment of the present invention is shown schematically in FIG. 1. The constituents for continuous production of the Grignard system, the solvent and the reactants, are introduced continuously to a plurality of reactors 10, 12 and 13. The reaction is exothermic and each reactor is cooled with internal cooling coils. The overflow product constituting the Grignard reagent is delivered to a surge product holding vessel 15 from which the useful product is continuously pumped, either to a storage tank or to the site where the Grignard reagent is used to promote organic synthesis.

The solvent for Grignard production, which may be tetrahydrofuran, is furnished from a supply vessel 20. The organohalide, which may be methyl chloride, is furnished from a separate supply vessel 21. The solvent and the organohalide are directed to the reactor vessels under pressure established by respective pumps 24 and 25, pumping these materials through conduits 26 and 27 which meet at a juncture 28 where the solvent and organohalide are combined as a mixture in a conduit 29. Conduit 29 is branched at 30 where part of the combined flow is directed to a conduit 31 which terminates at an inlet to reactor vessel 13. The remainder of the combined mixture is delivered through conduit 34 connected to the outlet of a circulation pump 35.

Conduit 34 delivers the mixture of solvent and organohalide to a heat exchanger 36 where the mixture, together with part of the reaction product from reactors 10 and 12, is subjected to cooling by forced circulation through the exchanger.

The materials passing through the heat exchanger are delivered to a conduit 37 which terminates at an inlet to reactor 12. Conduit 37 is branched at 38 by a conduit 39 connected to an inlet of reactor 10 which receives a mixture of solvent and organohalide.

Thus, it will be seen that the mixture of solvent and organohalide is delivered under pressure directly to reactor 13 through conduit 31 while the remaining part of the mixture of solvent and organohalide is delivered to the heat exchanger 36 and from thence under pressure to reactors 10 and 12.

Magnesium is furnished by a pair of supply hoppers 42 and 43. Magnesium is supplied in metered, incremental amounts to the respective vessels by gravity feed through supply lines 10-1, 12-1, 14-1 and 15-1. Each of these supply lines is equipped with a rotary valve 44 and/or a drop valve. The rate of delivery of magnesium to each supply line may be independently regulated by a timer control 45 which may be in the form of a variable speed motor for rotating the related valve 44 and/or incrementally adding small amounts of magnesium through the drop valves. In this connection it is appropriate to point out that the rate of delivery of solvent and the rate of delivery of organohalide may be independently regulated by flow rate control valves 47 and 48. The rate of delivery of organohalide is regulated to the rate of delivery of magnesium to the reactors 10, 12 and 13 so that magnesium is always in excess of the stoichiometric amount, the excess being approximately 3% molal concentration. In order to assure that any unreacted organohalide is consumed, magnesium may be fed to vessel 15 through supply line 15-1.

The contents in each of the vessels 10, 12, 13 and 15 is subjected to agitation to assure uniform distribution of the magnesium and therefore a substantially uniform product at levels within the reactors to be mentioned below. To this end, each of the reactors, and preferably the surge vessel as well, is equipped with a propeller 55 driven by a motor 56.

As mentioned above, vessel 15 is provided as a holding chamber, in effect, for the overflow surge product produced in reactors 10, 12 and 13. Accordingly, each reactor 10, 12 and 13 is tapped to enable the reaction product to overflow to the surge product or holding vessel. Thus, reactor 10 is provided with a conduit 58 opening into reactor 10 at a high point that sets the liquid level and allows overflow to vessel 15. In like manner reactor vessels 12 and 13 are tapped by conduits 61 and 62 connected to a manifold 63 which delivers the overflow product of reactors 12 and 13 to conduit 58 which itself becomes a manifold for delivering the final product from vessels 10, 12 and 13 to the surge or holding vessel 15.

Constant delivery of the product may be assured by constant feed of solvents and reactants into reactors 10, 12, and 13 where the reaction occurs, the product overflowing to reactor surge vessel 15.

The end product in vessel 15 flows into a drain conduit 65 connected to a delivery pump 66 which is responsible for pumping the end product, through conduit 67 to a point of delivery. The desired concentration of the end product may be regulated by pumping make-up solvent from a supply vessel 70 to a conduit 71 connected to conduit 67. A flow regulator control valve 72 is provided to enable the final concentration to be accurately determined.

As mentioned above, the exothermic output is quite large. In fact, the limiting factor in production is the ability to remove heat. Therefore, to avoid the industrial hazard of a runaway reaction and to control reaction rate, heat must be constantly withdrawn from the four vessels. Accordingly, each of the vessels 10, 12 13 and 15 is provided with internal coils 75 supplied with a coolant by means of a typical gas/liquid refrigeration unit 76. In order to reduce the demand on the compressors 52, and especially to permit a compressor to be idled as a spare from time to time, the external heat exchanger 36 is used to cool a recirculating section of the product produced in reactors 10 and 12. In accomplishing this the reactors 10 and 12 are provided with outlets below the overflow level to which conduits 78 and 79 are connected, in turn connected to a manifold 80 which supplies the inlet of pump 35. Consequently a part of the reacting content of reactors 10 and 12, and part of the reaction product as well, is withdrawn, pumped to the heat exchanger 36 and recirculated back to reactors 10 and 12 thereby enabling heat of reaction to be dissipated without depending entirely upon the capacity of the individual coolant systems which cool internally the vessels 10, 12, 13 and 15.

The system shown in FIG. 1 is capable of producing at the rate of twenty gallons per minute from each of the three reactors; production may be throttled to a low of ten gallons per minute. It will be recognized that by suitable valving and flow rate controls one reactor alone may be operated continuously to charge vessel 15 with an overflow product, but extension of the principle to two additional reactors results in increased production capacity and justifies use of an external heat exchanger which in time, especially during cooler days, permits one or more of the compressor units 76 to be idled and conserved.

The production rate can therefore be geared to the number of reactors in use and by the feed rate. FIG. 2 is a graph based on Table 1 below illustrating the amount of magnesium metal and methyl chloride necessary to obtain a usable Grignard at various feed rates of tetrahydrofuran. The concentration of Grignard varied from 2.10 millimoles per gram of system (Grignard plus solvent) to 2.40 millimoles per gram. The temperature of the reactors varied, proportionally, from 110° to 125° F.

TABLE 1

Grignard concentration: 2.10 mmoles per gram to 2.40 mmoles per gram; average 2.25 mmoles/gram
Temperatures of reactors: between 110° and 125° F

| THF Feed Rate | Magnesium | Methyl Chloride |
|---|---|---|
| 1 gpm | 30 lbs/hr | 60 lbs/hr |
| 10 gpm | 300 lbs/hr | 600 lbs/hr |
| 50 gpm | 1,500 lbs/hr | 3,000 lbs/hr |
| 100 gpm | 3,000 lbs/hr | 6,000 lbs/hr |

It will be seen from the foregoing that a Grignard reagent is continuously produced in a concentration easily determined by adding make-up solvent, if necessary, to the contents pumped from the holding vessel which receives the overflow product from one or more reactors to which magnesium is incrementally added in excess of the amount required to combine with the organohalide which is constantly supplied under pressure to the reactor together with the solvent. Reliance on an external heat exchanger enables the internal heat exchanger load to be conserved, recognizing that an extremely hot climatic condition may place a maximum demand on the regulating system 36 – 76.

It has been determined from reliable production data that magnesium losses due to the Wurtz-Fittig side reaction may be very substantially reduced by the continuous process of the present invention where it is possible to carefully control flow rates in all parts of the system to maintain excess magnesium. Thus, the continuous system enables the reaction to be conducted in the presence of an excess of magnesium, and therefore a low concentration of RX, while continuously removing the (overflow) final product at full concentration. This means, in effect, that a high concentration of RX which reduces the possibility of the Wurtz-Fittig side reaction within the reaction vessels compared to a batch operation where the Grignard concentration is constantly increasing, the magnesium is constantly decreasing, and higher and higher concentrations of RX must be added to drive the reaction to completion, bearing in mind that Wurtz-Fittig losses are a function of Grignard and RX concentrations as already noted. Also, the continuous process of the present invention is permissive of external cooling to extract heat, avoiding the "peaking" effect of the batch process where a great deal of heat is generated at the inception of the reaction which encourages the Wurtz-Fittig side reaction and solvent degradation.

Hence while we have illustrated and described a preferred embodiment of the present invention, it will be appreciated that variations and modifications may be adopted by those skilled in the art.

We claim:

1. Apparatus for continuous production of Grignard reagent comprising: a plurality of reaction vessels and a surge product holding vessel, pressurized supply means for constantly introducing into said reaction vessels a mixed stream of an organohalide and solvent under pressure, a supply hopper and feed means associated therewith positioned above each pair of reaction vessels for adding magnesium in incremental amounts to each of said vessels, overflow conduits each connected at one end to each of said vessels at a predetermined high level to afford escape for a Grignard system overflow product, means for collecting and transmitting the overflow product to said surge product holding vessel, a pump for constantly delivering the contents of the holding vessel for storage or use, a heat exchanger, and conduit means connected at one end to at least one of the reaction vessels at a high level considerably above the bottom thereof for receiving a reacting portion of the contents therefrom, said conduit means also being connected for circulating said reacting portion through the heat exchanger and back to said one reaction vessel.

2. Apparatus according to claim 1 wherein said conduit means is connected to said supply means so that said mixed stream joins said reacting portion being circulated to the heat exchanger.

3. Apparatus for continuous production of Grignard reagent comprising: a reaction vessel and a surge product holding vessel, a supply hopper and feed means associated therewith positioned above the reaction vessel for adding magnesium to said reaction vessel, an overflow conduit connected at one end to said reaction vessel and connected at the opposite end to the holding vessel to deliver a portion of the Grignard system product to said surge product holding vessel, means for delivering the contents of the holding vessel for storage or use, a heat exchanger located externally of the reaction vessel, another conduit connected at one end to the reaction vessel considerably above the bottom thereof for receiving, and further connected for circulating, a reacting portion of the contents of the reaction vessel through the heat exchanger and back to said reaction vessel, and means for introducing solvent and organohalide to the contents being circulated to the heat exchanger.

* * * * *